United States Patent
Belin et al.

(10) Patent No.: US 7,189,866 B2
(45) Date of Patent: Mar. 13, 2007

(54) SILOXANE POLYSULFIDE USABLE AS CROSS-LINKING AGENT, AND PROCESS FOR OBTAINING SUCH

(75) Inventors: Laure Belin, Riom (FR); Christiane Blanchard, Marsat (FR)

(73) Assignee: Michelin Recherche et Technique S.A., Granges-Paccot (CH)

( * ) Notice: Subject to any disclaimer, the term of this patent is extended or adjusted under 35 U.S.C. 154(b) by 0 days.

(21) Appl. No.: 10/945,813

(22) Filed: Sep. 21, 2004

(65) Prior Publication Data

US 2005/0090680 A1    Apr. 28, 2005

Related U.S. Application Data

(63) Continuation of application No. PCT/EP03/03905, filed on Apr. 15, 2003.

(30) Foreign Application Priority Data

Apr. 18, 2002 (FR) .................... 02 04964

(51) Int. Cl.
*C07F 7/04* (2006.01)
(52) U.S. Cl. ................................ 556/428
(58) Field of Classification Search ........... 556/428
See application file for complete search history.

(56) References Cited

U.S. PATENT DOCUMENTS 3,284,466 A * 11/1966 Rosenthal .................... 549/11

6,774,255 B1 * 8/2004 Tardivat et al. ............ 556/427

FOREIGN PATENT DOCUMENTS

CA    2425300    * 4/2002

OTHER PUBLICATIONS

FR0013254 Priority Document Oct. 13, 2000.*

* cited by examiner

*Primary Examiner*—Samuel Barts
(74) *Attorney, Agent, or Firm*—Cohen, Pontani, Lieberman & Pavane

(57) ABSTRACT

Siloxane polysulfide compound of the general formula (I) below:

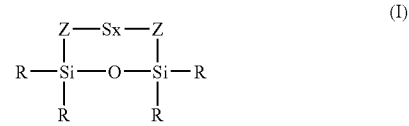

in which:
the number x, which may be an integer or a fractional number, is equal to or greater than 2;
the radicals Z, which may be identical or different, are divalent bond groups;
the radicals R, which may be identical or different, are hydrocarbon groups.

The use of such a compound as diene elastomer cross-linking agent, in particular in a rubber composition for a tire.

24 Claims, 4 Drawing Sheets

SILOXANE POLYSULFIDE USABLE AS CROSS-LINKING AGENT, AND PROCESS FOR OBTAINING SUCH

The present application is a continuation of International Application No. PCT/EP03/003905, filed Apr. 15, 2003, published in French with an English Abstract on Oct. 23, 2003 under PCT Article 21(2) as WO2003/087208, which claims priority to French Patent Application No. 02/04964, filed Apr. 18, 2002.

The present invention relates to cross-linking agents usable for cross-linking elastomeric networks, in particular in the manufacture of tires or semi-finished products for tires.

Since the discovery of the vulcanization or cross-linking of rubber by sulfur, numerous improvements have been made to the base process, but sulfur at present still remains the element which is indispensable from the industrial point of view for cross-linking diene elastomers.

The principle of vulcanization lies in the creation of sulfur bridges between two macromolecules by reaction on the double bonds of these diene elastomers. One of the striking characteristics of vulcanization is the simplicity with which this reaction can be controlled by adding compounds having an accelerating or retarding effect. By adjusting the respective amounts of sulfur and accelerators, it is in particular possible to control the vulcanization yield, to obtain sulfur bridges of different configurations which result, for a given rubber composition, in possible adjustments of the properties, both in the uncured state and in the cured state.

However, sulfur vulcanization has certain known drawbacks, including the problem of blooming in the uncured state, due to migration of the sulfur to the surface of the rubber articles in question, and above all limited resistance of the vulcanized rubber compositions in the cured state, due to the thermal ageing of the latter.

In particular, it is well known that vulcanized rubber compositions of diene elastomers which are cross-linked from sulfur are highly sensitive to temperature when the latter reaches a value close to the curing temperature or initial vulcanization temperature. The result is a drop in the density of the sulfur bridges formed initially upon vulcanization, the distribution of the vulcanization network evolving towards shortening, that is to say a reduction in the polysulfide bridges to the benefit of the monosulfide bridges. This phenomenon, which is known as "reversion", is accompanied by degradation of the mechanical properties of the vulcanized rubber composition.

Thus, the person skilled in the art is nowadays always in search of novel compounds which make it possible to overcome the aforementioned drawbacks, in particular to cross-link the chains of diene elastomers while providing better thermal stability.

Now, the Applicants have during their research discovered certain novel compounds, of the siloxane type, which unexpectedly make it possible to vulcanize or cross-link the rubber compositions without any addition of sulfur, while providing the vulcanized rubber compositions with improved reversion resistance. These compounds furthermore do not have the aforementioned problem of blooming.

Consequently, a first subject of the invention relates to a siloxane polysulfide compound of the general formula (I) below:

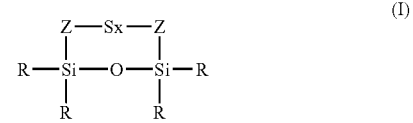

in which:
- the number x, which may be an integer or a fractional number, is equal to or greater than 2;
- the radicals Z, which may be identical or different, are divalent bond groups preferably comprising from 1 to 18 carbon atoms;
- the radicals R, which may be identical or different, are hydrocarbon groups preferably comprising from 1 to 18 carbon atoms.

The siloxane polysulfide according to the invention is capable of being prepared by a process which constitutes another subject of the invention, said process comprising the following steps (x, Z and R having the above meanings):

a) starting from a halogenated organosilane (hereafter product A) of formula (Hal=halogen):

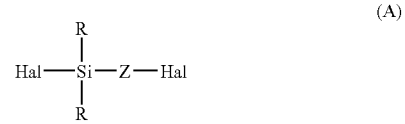

b) subjecting it either to alcoholysis by action of an alcohol R'—OH (R'=hydrocarbon radical) or to hydrolysis by action of water in an inert organic solvent, in both cases in the presence of an organic base to trap the acid halide formed, in order to obtain (hereafter product B) either a monoalkoxysilane (in this case, R' is the hydrocarbon radical in formula (B)), or a monohydroxysilane (in this case, R' is H in formula (B)), of formula:

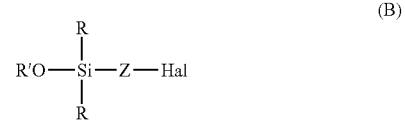

c) sulfurizing product B by action of a polysulfide, in order to obtain as intermediate product (hereafter product C) an alkoxysilane or hydroxysilane polysulfide of formula:

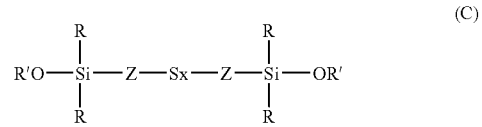

d) then performing a cyclization step on product C to produce the desired product of formula (I):

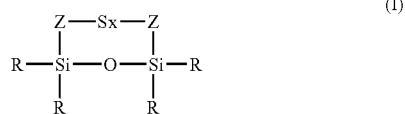

(I)

Another subject of the invention is the use as cross-linking agent, in a rubber composition based on diene elastomer and a reinforcing filler, of a siloxane polysulfide of formula (I) above.

I. MEASUREMENTS AND TESTS USED

Figure 1:
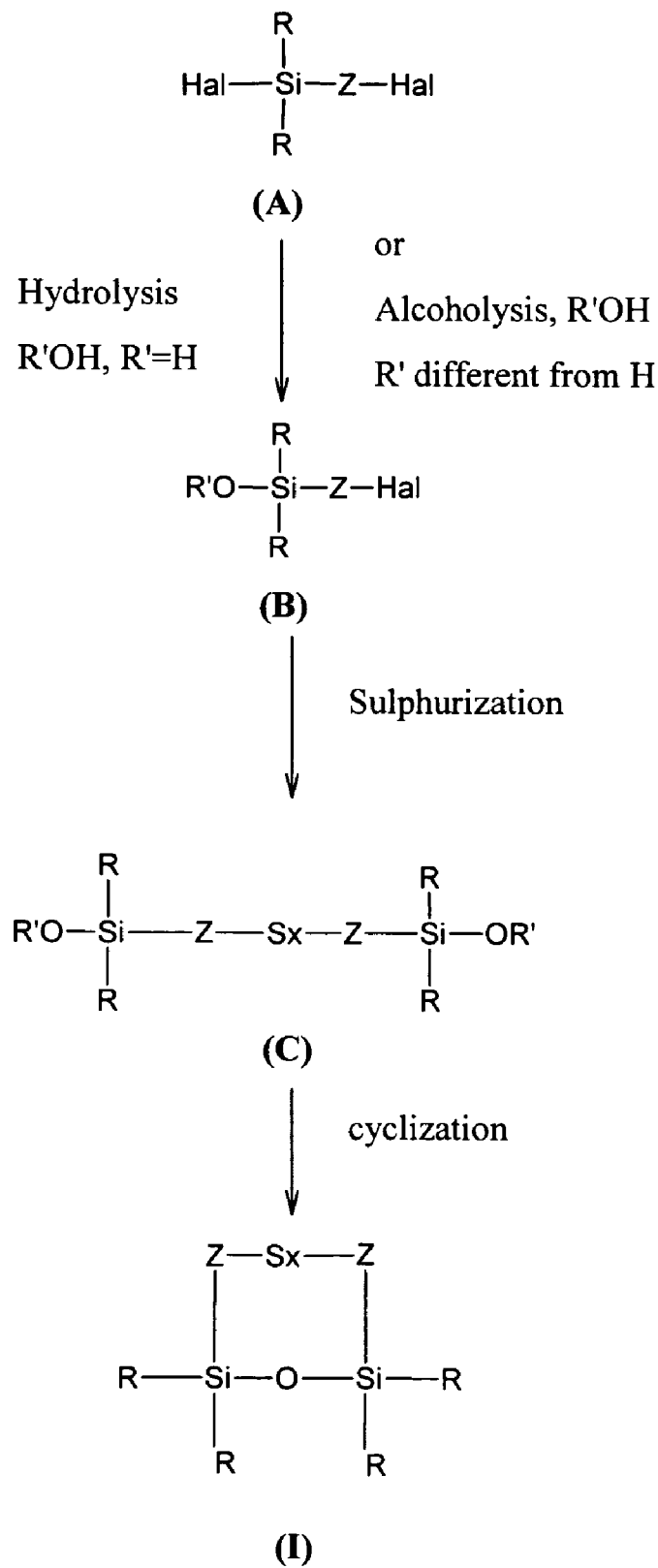
FIG. 1 shows a first process for obtaining a siloxane polysulphide.

The rubber compositions in which the siloxane polysulfides are tested are characterized, before and after curing, as indicated below.

I-1. Mooney Plasticity

An oscillating consistometer such as described in French Standard NF T 43-005 (1991) is used. The Mooney plasticity is measured in accordance with the following principle: the raw composition (i.e. before curing) is moulded in a cylindrical enclosure heated to 100° C. After one minute's preheating, the rotor turns within the test piece at 2 rpm, and the torque used for maintaining this movement is measured after 4 minutes' rotation. The Mooney plasticity (ML 1+4) is expressed in "Mooney units" (MU, with 1 MU=0.83 N.m).

I-2. Scorching Time

The measurements are effected at 130° C., in accordance with French Standard NF T 43-005 (1991). The evolution of the consistometric index as a function of time makes it possible to determine the scorching time for the rubber compositions, assessed in accordance with the above standard by the parameter T5 (case of a large rotor), expressed in minutes, and defined as being the time necessary to obtain an increase in the consistometric index (expressed in MU) of 5 units above the minimum value measured for this index.

I-3. Rheometry

The measurements are effected at 150° C. or at 165° C., depending on the case, with an oscillating-chamber rheometer, in accordance with DIN Standard 53529—part 3 (June 1983). The evolution of the rheometric torque as a function of time describes the evolution of the stiffening of the composition following the vulcanization reaction (see attached FIG. 4). The measurements are processed in accordance with DIN Standard 53529—part 2 (March 1983): the minimum and maximum torques, measured in dN.m (deciNewton.meters), are referred to respectively as $C_{min}$ and $C_{max}$; $t_i$ is the induction delay, that is to say, the time necessary for the start of the vulcanization reaction. The deviation $\Delta$Torque (in dN.m) is also measured between $C_{max}$ and $C_{min}$, which makes it possible to assess the vulcanization yield.

The mechanical or dynamic properties indicated hereafter (sections I-4 and I-5) are those measured at the "curing optimum", that is to say, in known manner, those obtained, for a given curing temperature, after the minimum curing time to obtain the maximum rheometric torque $C_{max}$.

I-4. Tensile Tests

These tests make it possible to determine the elasticity stresses and the properties at break. Unless indicated otherwise, they are effected in accordance with French Standard NF T 46-002 of September 1988. The nominal secant moduli (or apparent stresses, in MPa) at 10% elongation (ME10), 100% elongation (ME100) and 300% elongation (ME300) are measured in a second elongation (i.e. after a cycle of accommodation to the amount of extension provided for the measurement itself). The breaking stresses (in MPa) and the elongations at break (in %) are also measured. All these tensile measurements are effected under normal conditions of temperature (23±2° C.) and humidity (50±5% relative humidity), in accordance with French Standard NF T 40-101 (December 1979).

I-5. Dynamic Properties

The dynamic properties $\Delta G^*$ and $\tan(\delta)_{max}$ are measured on a viscoanalyser (Metravib VA4000), in accordance with Standard ASTM D 5992-96. The response of a sample of vulcanized composition (cylindrical test piece of a thickness of 4 mm and a section of 400 mm$^2$), subjected to an alternating single sinusoidal shearing stress, at a frequency of 10 Hz, under normal conditions of temperature (23° C.) in accordance with Standard ASTM D 1349-99, is recorded. Scanning is effected at an amplitude of deformation of 0.1 to 50% (outward cycle), then of 50% to 1% (return cycle). The results used are the complex dynamic shear modulus ($G^*$) and the loss factor $\tan(\delta)$. For the return cycle, the maximum value of $\tan(\delta)$ which is observed, $\tan(\delta)_{max}$, is indicated, as is the deviation in the complex modulus ($\Delta G^*$) between the values at 0.15 and 50% deformation (Payne effect).

I-6. Measurement of the Reversion

The reversion may be analysed using different methods, the aim being to determine, indirectly, the evolution of the density of the sulfur bridges, between curing at the optimum ($C_{max}$) and prolonged curing.

The first approach consists of measuring the evolution of the rheometric torque: the parameters $\Delta R_{60}$ and $\Delta R_{120}$ represent the evolution in % of the torque between $C_{max}$ and the torque measured after 60 or 120 minutes curing, respectively, at a given curing temperature (for example 150° C. or 165° C.).

The second approach consists of measuring the evolution of the moduli ME100 or ME300: the parameters $\Delta$ME100 and $\Delta$ME300 correspond to the evolution in % of the respective moduli between the curing optimum ($C_{max}$) and after prolonged curing of 2 hours, at a given curing temperature (for example 150° C. or 165° C.).

II. CONDITIONS OF IMPLEMENTATION OF THE INVENTION

In the present description, unless expressly indicated otherwise, all the percentages (%) indicated are mass %.

II-1. Siloxane Polysulfide of the Invention

The first subject of the invention is therefore a siloxane polysulfide of the aforementioned formula (I):

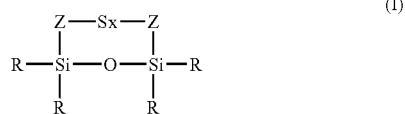
(I)

in which:
- the number x, which may be an integer or a fractional number, is equal to or greater than 2;
- the radicals Z, which may be identical or different, are divalent bond groups preferably comprising from 1 to 18 carbon atoms;
- the radicals R, which may be identical or different, are hydrocarbon groups preferably comprising from 1 to 18 carbon atoms.

This compound is characterized by the presence, in its molecule, of a polysulfide group $S_x$ (with $x \geq 2$, that is to say including the disulfide group) linked via two silicon atoms to form a di-siloxane structure (ring)≡Si—O—Si≡. It may therefore be described as a cyclic di-siloxane polysulfide.

The radicals R, which may be straight-chain or branched, preferably comprising from 1 to 18 carbon atoms, are more preferably selected from among alkyls, cycloalkyls or aryls, in particular from among $C_1$–$C_6$ alkyls, $C_5$–$C_8$-cycloalkyls and the phenyl radical; these alkyl, cycloalkyl or phenyl groups may also contain heteroatoms such as N, O or S.

Of these radicals R, mention will be made in particular, by way of example, of those selected from the group consisting of methyl, ethyl, n-propyl, isopropyl, n-butyl, sec.-butyl, tert.-butyl, n-pentyl, neopentyl, n-hexyl, 2-ethylhexyl, n-octyl, iso-octyl, cyclopentyl, cyclohexyl, 2-methylcyclohexyl, phenyl, toluyl and benzyl. More preferably still, the radicals R, which may be identical or different, are $C_1$–$C_3$ alkyls (namely methyl, ethyl, n-propyl, isopropyl), very particularly selected from among methyl and ethyl.

The radicals Z, which may be substituted or not substituted, comprising preferably 1 to 18 carbon atoms, are preferably hydrocarbon radicals, whether saturated or not saturated, these radicals Z possibly being interrupted within the hydrocarbon chain by at least one heteroatom such as O, S or N. In particular $C_1$–$C_{18}$ alkylene groups or $C_6$–$C_{12}$ arylene groups, more particularly $C_1$–$C_{10}$ alkylenes, are suitable.

Particularly preferred compounds of formula (I) are those in which the radicals R, which may be identical or different, are $C_1$–$C_3$ alkyl groups and the radicals Z, which may be identical or different, are $C_1$–$C_4$ alkylenes (methylene, ethylene, propylene, butylene), in particular $C_2$–$C_{14}$ alkylenes, with x more preferably being greater than 2.

Of the latter, mention will very particularly be made of the cyclic tetramethyl-disiloxane polysulfide of the formula (II) (i.e. R=methyl):

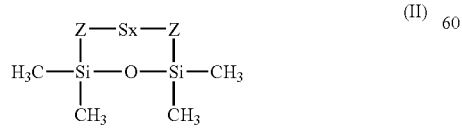
(II)

in which, preferably, "x" has an average value of between 3 and 5, more preferably close to 4 (that is to say of between 3.5 and 4.5) and Z is a $C_2$–$C_4$ alkylene.

By way of a particular example of the compound of formula (II), mention will be made in particular of that of structural formula (II-1) hereafter, in which Z represents the propylene group:

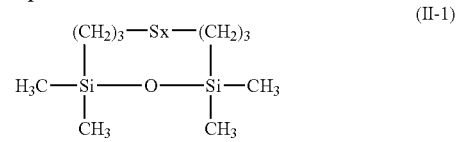
(II-1)

In formulae (I) and (II) above, the number x of sulfur atoms may vary to a great extent, for example from 2 to 9, depending on the specific synthesis conditions for the polysulfide; however, the values of x are preferably selected within a range from 2 (disulfides) to 6 (hexasulfides), passing via the corresponding trisulfides (x=3), tetrasulfides (x=4) and pentasulfides (x=5). More preferably still, x is selected between 3 and 5, more particularly close to 4 (that is to say between 3.5 and 4.5).

These siloxane polysulfides of the invention may be prepared using a novel synthesis process which constitutes another subject of the present invention.

II-2. Synthesis Process

The process according to the invention, for preparing a siloxane polysulfide of formula (I), is illustrated diagrammatically in the appended FIG. 1. It comprises the following steps (x, Z and R having the above meanings):

a) the starting point is a halogenated organosilane (hereafter product A) of formula (A) (Hal=halogen):

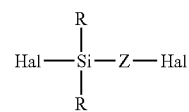

b) it is subjected either to alcoholysis by action of an alcohol R'—OH (R'=hydrocarbon radical), or hydrolysis by action of water in an inert organic solvent, in both cases in the presence of an organic base to trap the acid halide formed, in order to obtain (hereafter product B) either a monoalkoxysilane (in this case, R' is the hydrocarbon radical in formula (B)), or a monohydroxysilane (in this case, R' is H in formula (B)), of formula (B):

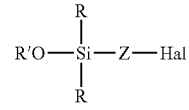

c) a sulfurization step is performed on product B by action of a polysulfide, in order to obtain as intermediate product (hereafter product C) an alkoxysilane or hydroxysilane polysulfide of formula (C):

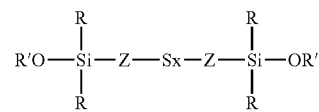

d) then a cyclization step is performed on product C to produce the desired product of formula (I):

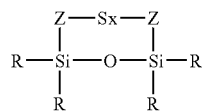

The halogens (Hal) of the starting silane (product A) may be identical or different, preferably selected from among bromine and chlorine; more preferably chlorine is used. Generally, the starting halosilanes (products A) and their intermediate derivatives (products B or C) are liquid products; they may therefore be used as such or alternatively in the diluted state in an appropriate solvent, when implementing the different steps of the process of the invention.

The hydrolysis step for product A, if applicable, is carried out directly on the starting halogenated silane (product A), by action of water in an inert organic solvent, for example an ether, and in the presence of an organic base intended to trap the acid halide formed.

The alcoholysis step of product A for its part consists of substituting the halogen (Hal) borne by the silicon atom of product A with the alkoxyl group (OR') of an alcohol, in the presence of an organic base intended to trap the acid halide released during the reaction. The hydrocarbon radical R' of the alcohol (R'—OH) preferably comprises from 1 to 8 carbon atoms, and is more preferably selected from among $C_1$–$C_6$ alkyls, more preferably still from among $C_1$–$C_3$ alkyls, in particular methyl or ethyl. An amine, preferably a tertiary amine such as triethylamine, may be used as organic base intended to trap the acid halide formed. In order better to trap the acid halide, the alcoholysis is carried out at a temperature which is preferably less than 15° C., more preferably less than 10° C.

For the sulfurization step, in particular an ammonium or metal polysulfide ($x \geq 2$), of formula $M_2S_x$ or $M'S_x$ (M=alkali metal or $NH_4$; M'=Zn or alkaline-earth metal) may be used; examples of such compounds are polysulfides of Na, K, Cs, Rb, Ca, Mg, Zn and $NH_4$, x being preferably within a range from 2 to 6, more preferably from 3 to 5 (in particular between 3.5 and 4.5). Preferably a sodium polysulfide $Na_2S_x$ is used, in particular $Na_2S_2$, $Na_2S_3$, $Na_2S_4$, $Na_2S_5$, $Na_2S_6$, this polysulfide preferably being generated by the action of sulfur ($S_8$) on $Na_2S$. In known manner, the preparation of such a polysulfide is carried out in a solvent, whether organic or not, such as for example water, alcohols, ketones or ethers, in which solvents the reagents are partially or totally soluble.

However, it is preferred to perform the sulfurization step in the absence of any alcohol; operation is then preferably in the aqueous phase, more preferably in a two-phase medium water/organic solvent (for example toluene, xylene, benzene, heptane or equivalent), as described for example in EP-A-694 552 or U.S. Pat. No. 5,405,985 relating to the synthesis of polysulfurized alkoxysilanes. The reaction is then preferably carried out in the presence of a phase transfer catalyst to which is more preferably added a salt of formula M"Hal or M"$SO_4$, M" being selected from among Li, Na and K, and Hal being selected from among F, Cl and Br. The salt used is then preferably selected from among NaCl, NaBr and $Na_2SO_4$; even more preferably, NaCl is used. The quantity of salt may vary for example from 10% by weight of the aqueous solution to complete saturation of the solution. The phase transfer catalyst is for example tetrabutylammonium bromide (TBAB).

The sulfurization step is preferably carried out under inert gas such as argon. The temperature of the reaction medium is not critical, and it is for example possible to work at ambient temperature; it is however preferred to operate in the hot state to increase the reaction rate, for example between 60° C. and 100° C. or even up to the boiling point of the solvent. The molar ratio of the hydroxysilane or alkoxysilane (product B) to the polysulfide is preferably adjusted so as to have a slight excess of polysulfide relative to the stoichiometric quantity.

If the sulfurization is carried out in the organic phase, product B is itself preferably pre-diluted in the inert organic solvent such as an alcohol, a ketone or an ether. When the reaction is finished, the resulting salt (metal halide) is filtered off and the organic solvent is removed from the filtrate by vacuum distillation. In the case of sulfurization in the aqueous phase or two-phase (water/organic solvent) sulfurization, if applicable the organic phase containing product C is isolated and the reaction solvent followed by the unreacted reagent B are distilled in succession in a vacuum.

The cyclization step on product C is performed differently according to whether it is a hydroxysilane polysulfide, in this case by a condensation step preferably catalysed by the presence of an acid or of a base, or alternatively an alkoxysilane polysulfide, in this case by an acid or basic hydrolysis step, preferably of acid type. To carry out this cyclization step, for example product C, diluted in an organic solvent, is introduced into a mixture consisting of an appropriate quantity of water, for example at a rate of two molar equivalents relative to the polysulfide which is reacted, and a catalytic quantity of catalyst such as an organic acid such as a carboxylic acid, more particularly trifluoroacetic acid.

The siloxane polysulfides synthesised in accordance with the process described above are in fact mixtures of polysulfides (for example from x=2 to x=9), with consequently an average value for x which is other than an integer.

II-3. Use as Cross-linking Agent

The siloxane polysulfides previously described have proved sufficiently effective on their own for cross-linking diene elastomers.

They may advantageously replace, in the compositions of such elastomers, all the sulfur and other conventional sulfur donor(s) in the compositions of such elastomers. They are then used, in these compositions, in a preferred amount greater than 0.5 phr, more preferably of between 1 and 15 phr, in particular between 3 and 12 phr (phr=parts by weight per hundred of elastomer).

Although this is not limitative, they may be used, by way of example, for cross-linking rubber compositions intended for the manufacture of tires, based on at least a diene elastomer and a reinforcing filler in an amount of for example between 30 and 150 phr.

For such a use, the diene elastomer is then preferably selected from the group of highly unsaturated diene elastomers which consists of polybutadienes (BR), natural rubber (NR), synthetic polyisoprenes (IR), butadiene copolymers (in particular butadiene/styrene (SBR), butadiene/isoprene (BIR), butadiene/acrylonitrile (NBR)), isoprene copolymers (in particular isoprene/styrene (SIR) or butadiene/styrene/isoprene copolymers (SBIR)), and mixtures of these elastomers.

Any type of reinforcing filler known for its ability to reinforce a rubber composition usable for the manufacture of tires may be used, for example an organic filler such as carbon black or alternatively a reinforcing inorganic filler such as silica, with which a coupling agent will then be associated. Suitable carbon blacks are all the carbon blacks, particularly blacks of the type HAF, ISAF and SAF, conventionally used in tires (what are called tire-grade blacks), for example in treads for these tires. Of the latter, reference will more particularly be made to the reinforcing carbon blacks of series 100, 200 or 300 (ASTM grades), such as, for example, the blacks N115, N134, N234, N330, N339, N347, N375. Suitable reinforcing inorganic fillers are in particular mineral fillers of siliceous or aluminous type, in particular silica ($SiO_2$). The silica used may be any reinforcing silica known to the person skilled in the art, in particular any precipitated or fumed silica having a BET surface area and a specific CTAB surface area both of which are less than 450 $m^2/g$, preferably from 30 to 400 $m^2/g$. Highly dispersible precipitated silicas (referred to as "HD") are preferred, in particular when the invention is used for the manufacturing of tires having a low rolling resistance. Any known coupling agent, in particular organosilanes or polyorganosiloxanes which are at least bifunctional, can be used for coupling the reinforcing inorganic filler to the diene elastomer.

With the siloxane polysulfide previously described there is preferably associated, in its cross-linking function, a primary vulcanization accelerator, in a preferred amount of between 0.1 and 5 phr, more preferably of between 0.5 and 3 phr.

In particular accelerators of the thiazole type are suitable, as are their derivatives of formula (III):

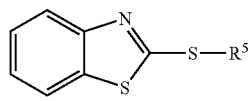
(III)

in which $R^5$ represents a hydrogen atom, a 2-mercaptobenzothiazyl group of formula (IV):

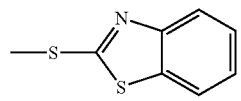
(IV)

or alternatively a group of formula (V):

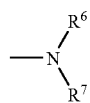
(V)

in which $R^6$ and $R^7$ represent independently a hydrogen atom, a 2-mercaptobenzothiazyl group (formula IV), a $C_1$–$C_4$ alkyl group or a $C_5$–$C_8$ cycloalkyl group, comprising preferably 6 units, said ring possibly comprising at least one heteroatom such as S, O or N.

Thiazole accelerators and preferred derivatives are in particular selected from the group consisting of 2-mercaptobenzothiazole, 2-mercaptobenzothiazyl disulfide, N-cyclohexyl-2-benzothiazyl sulfenamide, N,N-dicyclohexyl-2-benzothiazyl sulfenamide, N-tert.-butyl-2-benzothiazyl sulfenamide, N-cyclohexyl-2-benzothiazyl sulfenimide, N-tert.-butyl-2-benzothiazyl sulfenimide and mixtures of these compounds.

Suitable accelerators are also the compounds of the family of thiurams (formula VI) and zinc dithiocarbamate derivatives (formula VII):

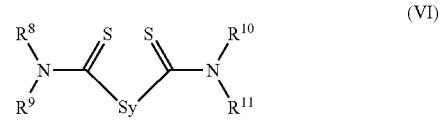
(VI)

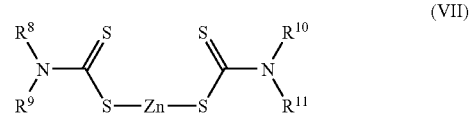
(VII)

in which y varies from 1 to 4, and is more particularly equal to 1 or 2; $R^8$, $R^9$, $R^{10}$ and $R^{11}$ each represent independently an alkyl group comprising from 1 to 8 carbon atoms, a benzyl group, a combination of $R^8$ and $R^9$ and a combination of $R^{10}$ and $R^{11}$ to form a cyclic pentamethylene group or a cyclic methyl-pentamethylene group and in which $R^8$ and $R^9$ and $R^{10}$ and $R^{11}$ are joined together.

Accelerators of thiuram type are in particular selected from the preferred group consisting of tetramethylthiuram monosulfate, tetramethylthiuram disulfide, tetraethylthiuram disulfide, tetrabutylthiuram disulfide, tetra-isobutylthiuram disulfide, tetrabenzylthiuram disulfide and mixtures of these compounds. Among these, tetrabenzylthiuram disulfide is more preferably used.

By way of other examples of accelerators usable according to the invention, mention will be made of zinc dithiocarbamates, in particular zinc tetramethyl dithiocarbamate, zinc tetraethyl dithiocarbamate and zinc tetrabenzyl dithiocarbamate. Of these, zinc tetrabenzyl dithiocarbamate is more preferably used.

To conclude, the primary vulcanization accelerators used in the context of the present invention are even more preferably selected from the group consisting of 2-mercaptobenzothiazyl disulfide (abbreviated to "MBTS"), N-cyclohexyl-2-benzothiazyl sulfenamide (abbreviated to "CBS"), N,N-dicyclohexyl-2-benzothiazyl sulfenamide (abbreviated to "DCBS"), N-tert.-butyl-2-benzothiazyl sulfenamide (abbreviated to "TBBS"), N-tert.-butyl-2-benzothiazyl sulfenimide (abbreviated to "TBSI") and mixtures of these compounds.

III. EXAMPLES OF EMBODIMENT OF THE INVENTION

In the examples of embodiment which follow, the invention is carried out with the cyclic polysulfurized tetramethyldisiloxane of specific formula (II-1) hereafter:

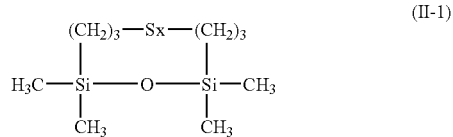
(II-1)

III-1. Synthesis of the Siloxane Polysulfide

The product above of formula (II-1) (hereafter referred to as product D) is synthesised, in the following examples, according to the two different processes illustrated diagrammatically in FIG. 1 (hydrolysis or alcoholysis).

A) Synthesis 1 (Hydrolysis)

Figure 2:
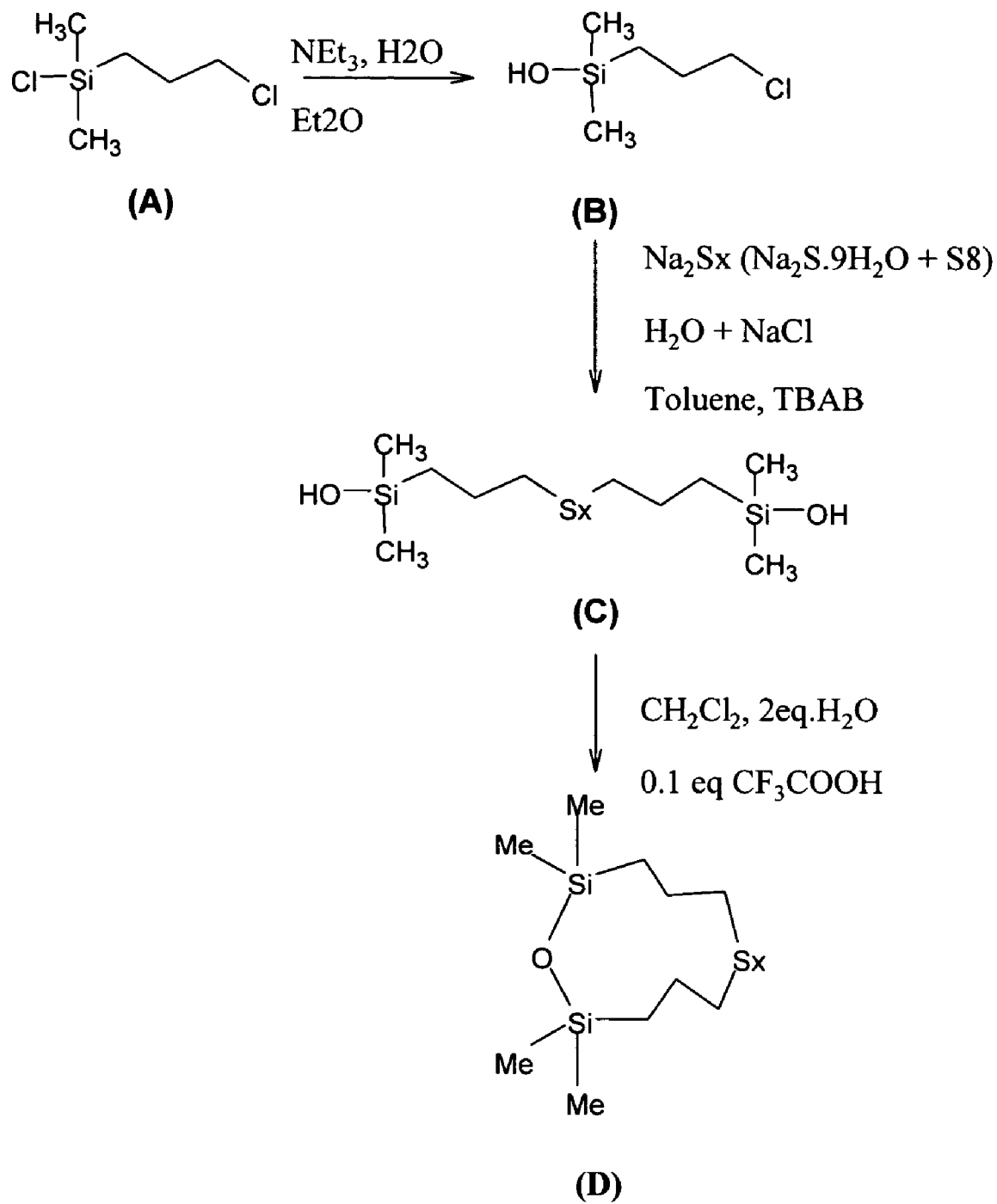
FIG. 2 shows a second process for obtaining a siloxane polysulphide.

Product D is synthesised using a process according to the invention consisting of several steps, starting from chloropropyl dimethylchlorosilane (hereafter referred to as product A), via chloropropyl dimethylsilanol (hereafter referred to as product B) and bis-(propyldimethylsilanol) polysulfide (hereafter referred to as product C). The synthesis equation applied is the one shown in the appended FIG. 2.

a) Preparation of the Chloropropyl Dimethylsilanol (Product B)

As has been explained previously, product B may be prepared directly by hydrolysis of the starting product A, in an inert organic solvent (ether), in the presence of water as hydroxyl donor and triethylamine intended to trap the released hydrochloric acid. Preferably an excess of water is introduced so as to promote the desired reaction, and to avoid the condensation reaction of the silanol generated on the added chlorosilane. Using a slight excess of triethylamine will ensure that all the hydrochloric acid is trapped, the residual triethylamine being distilled once the reaction has ended.

The procedure is more precisely as follows.

9.78 ml of triethylamine (70.1 mmol, or 1.5 equivalents relative to product A), 3.36 g of water (187 mmol, or 4 equivalents relative to product A) then 150 ml of ether are introduced into a 500 ml three-necked flask, surmounted by a condenser and provided with magnetic stirring. This solution is cooled using an ice bath, to a temperature less than 10° C., before slowly adding a solution of product A (8.0 g, or 46.7 mmol in 80 ml ether). The immediate appearance of a white precipitate is observed, which corresponds to the triethylamine chlorohydrate. Once the addition of product A has ended, the stirring of the reaction medium is continued for 30 min, it remaining at a temperature of less than 10° C. The precipitate formed is then filtered off and the collected filtrate is dried on magnesium sulfate, filtered then concentrated in a vacuum. The residual triethylamine is distilled off. Thus 6.1 g of a vivid yellow liquid which corresponds, according to NMR and mass spectrometry analysis, to the desired product B (purity of the product greater than 95%) is collected.

b) Preparation of the bis(propyldimethylsilanol)polysulfide (Product C)

In this step, the sodium polysulfide, produced by insertion of sulfur into sodium sulfide $Na_2S$ in aqueous medium, substitutes the chlorine atom of two molecules of product C in solution in toluene. The reaction is carried out in the presence of a phase transfer catalyst (TBAB) and sodium chloride NaCl.

4.01 g (or 16.7 mmol) of $Na_2S.9H_2O$ and 1.60 g (or 50.1 mmol) of sulfur which are dissolved in 40 ml of an aqueous solution of NaCl (5.73 g, or 98.2 mmol) and 8 ml of toluene are introduced into a 250 ml three-necked flask, surmounted by a condenser and provided with magnetic stirring. This mixture is heated to 85° C.; it is observed, upon the increase in temperature, that the reaction medium changes colour from yellow to dark red.

Once the operating temperature has been reached, 0.286 g of TBAB (or 0.88 mmol) is introduced in a single go, then the drop by drop addition of product B (5.0 g, or 32.7 mmol) in solution in 30 ml of toluene is begun. During the addition, the toluene phase has a vivid red coloration which turns gradually to orange, whereas the initially vivid red aqueous phase becomes paler and finally colourless and clear, once the pouring has ended. The reaction is thus continued for 75 min, at the temperature of 85° C., then the reaction medium is cooled under argon.

The reaction medium is then transferred into a separating funnel so as to isolate the toluene phase, which is dried over magnesium sulfate after having been washed with water. The organic solution is then filtered and taken up again in ether before being distilled in a ball oven (40° C.), in order to remove the residual chloropropyl dimethylsilanol (product B).

Finally 3.92 g of a viscous orange liquid is collected, NMR and mass spectrometry analysis of which confirms the majority presence of bis-(propyldimethylsilanol)polysulfide—product C—accompanied by traces of the starting product and of product D.

c) Preparation of the Cyclic tetramethyl-disiloxane Polysulfide (Product D)

0.24 g of water (2 equivalents, or 13.4 mmol) and a catalytic quantity of trifluoroacetic acid (0.1 equivalent, or 0.67 mmol), to which is added 2 g of product C diluted in 18 ml of dichloromethane, are introduced into a 100 ml three-necked flask.

The reaction medium is kept stirred for 24 hours before being dried on magnesium sulfate, filtered and concentrated in a vacuum.

1.8 g of product D is collected, the structure below of which is confirmed by NMR analysis:

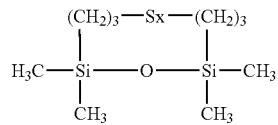

The product D thus synthesised is in fact formed of a distribution of polysulfides, from the disulfide (x=2) to the hexasulfide (x=6), centred on an average value close to 4.0 (x=3.9). The amount of disulfide $S_2$, determined by NMR, is equal to approximately 18% of the polysulfide units.

The person skilled in the art will understand that modified synthesis conditions would make it possible to obtain other distributions of polysulfides, with average values of x which are variable but preferably between 3 and 5.

B) Synthesis 2 (Alcoholysis)

Figure 3:
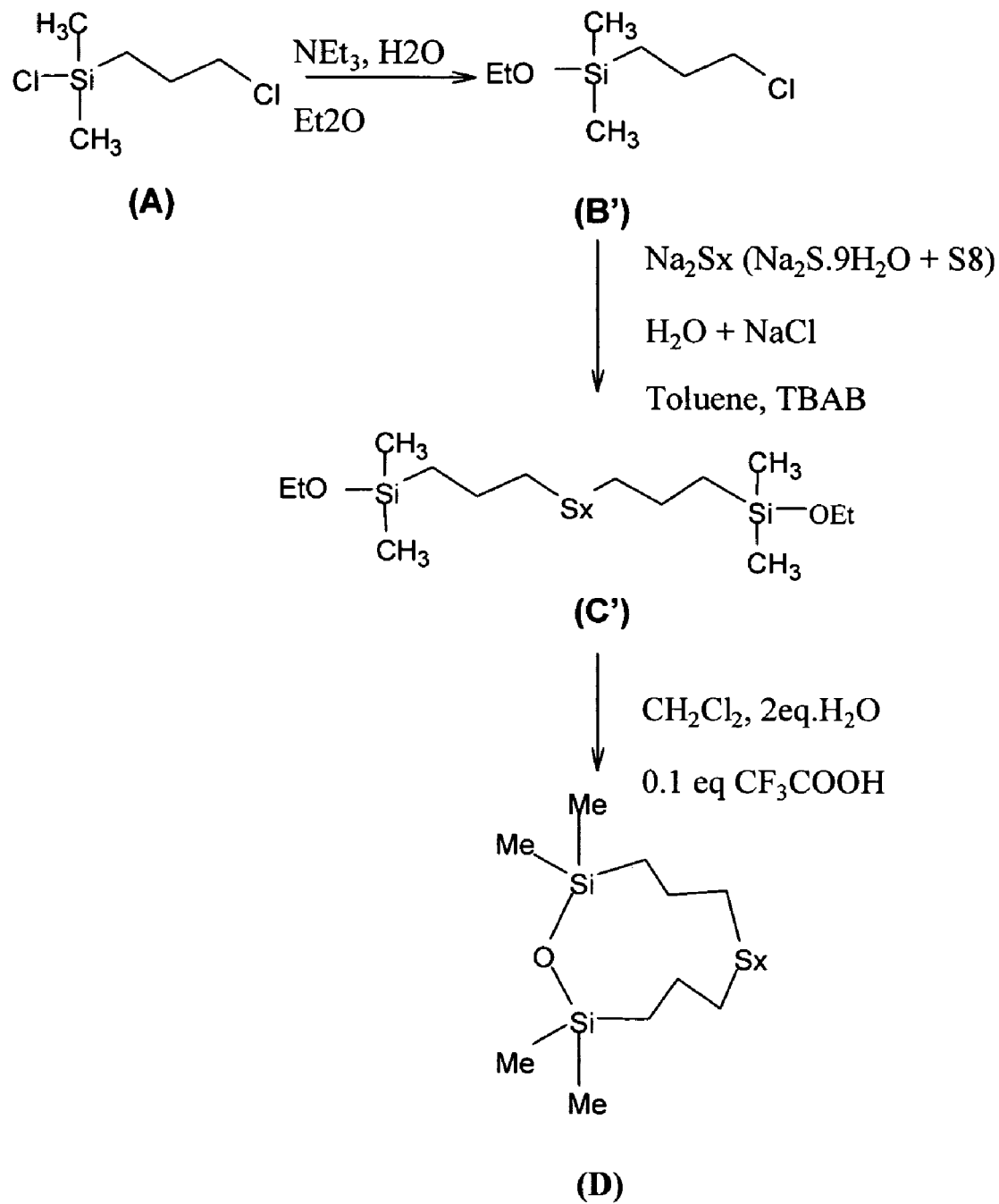
FIG. 3 shows a third process for obtaining a siloxane polysulphide.

Product D is synthesised using another process according to the invention consisting of several steps, starting from chloropropyl dimethylchlorosilane (product A), via chloropropyl dimethylethoxysilane (product B') and bis-(propyldimethylethoxysilane) polysulfide (product C'). The synthesis equation applied is the one shown in the appended FIG. 3.

a) Preparation of the chloropropyl dimethylethoxysilane (Product B')

The first step consists of alcoholysis making it possible to substitute the chlorine borne by the silicon atom of product A with an ethoxyl group of ethanol, this reaction being carried out in the presence of triethylamine intended to trap the hydrochloric acid released during the reaction.

The procedure is more precisely as follows.

950 ml of ethanol (grade Normapur) then 288 ml of triethylamine (2.07 mol, or 209 g) is introduced, using a syringe, under a current of argon, into a 2 l three-necked flask (dried in an oven for 24 h beforehand), surmounted by a condenser and provided with magnetic stirring. The mixture is then cooled to a temperature of approximately 5° C., before the addition of product A (237.7 g, or 1.38 mol—product from ABCR sold under the reference SIC2336.0) is begun, it being carried out using a peristaltic pump; the hydrochloric acid released is immediately trapped by the triethylamine, forming triethylamine chlorohydrate.

Once the pouring has ended (after approximately 8 h), the ice bath is removed, while the stirring is continued at ambient temperature throughout the night, under a current of argon. After eight hours, GPC (gas phase chromatography) analysis shows that the peak corresponding to the starting product A has disappeared and that the chloropropyl dimethylethoxysilane (product B') has formed. The reaction medium is then filtered through an Allihn condenser to separate product B' in solution in ethanol from the triethylamine chlorohydrate.

The filtrate containing the product B' is concentrated then distilled in a vacuum (2 mm Hg; oil bath temperature 70° C.; temperature at head of column 45° C.), in order to remove the excess free triethylamine and isolate the product B' in the pure state. Thus 160 g of a colourless liquid, NMR and mass spectrometry analyses of which confirm that it is in fact the desired product B', is collected.

b) Preparation of the bis(propyldimethylethoxysilane) polysulfide (Product C')

In this step, the sodium polysulfide, produced by insertion of sulfur into sodium sulfide $Na_2S$ in aqueous medium, substitutes the chlorine atom of two molecules of product B' in solution in toluene. The reaction is carried out in the presence of a phase transfer catalyst (TBAB) and sodium chloride NaCl.

3.50 g (or 14.5 mmol) of $Na_2S.9H_2O$ and 1.40 g (or 43.7 mmol) of sulfur which are dissolved in 40 ml of an aqueous solution of NaCl (5.0 g, or 85.8 mmol) and 8 ml of toluene are introduced into a 250 ml three-necked flask, surmounted by a condenser and provided with magnetic stirring. This mixture is heated to 85° C.; it is observed, upon the increase in temperature, that the reaction medium changes colour from yellow to dark red.

Once the operating temperature has been reached, 0.25 g of TBAB (or 0.77 mmol) is introduced in a single go, then the drop by drop addition of product (B') is begun (5.17 g, or 28.6 mmol) in solution in 30 ml of toluene. During the addition, the toluene phase has a vivid red coloration which turns gradually to orange, whereas the initially vivid red aqueous phase becomes paler and finally colourless and clear, once the pouring has ended. The reaction is thus continued for 75 min, at the temperature of 85° C., then the reaction medium is cooled under argon.

The reaction medium is then decanted into a separating funnel so as to isolate the toluene phase, which is dried over magnesium sulfate after having been washed with water. The organic solution is then filtered and taken up again in ether before being distilled in a ball oven (40° C.), in order to remove the residual chloropropyl dimethylethoxysilane (product B'), namely 0.52 g. Finally 3.84 g of a viscous red-orange liquid are collected, NMR and mass spectrometry analysis of which confirms the majority presence of bis-(propyldimethylethoxysilane) polysulfide accompanied by traces of the starting product.

c) Preparation of the Cyclic Polysulfurized tetramethyldisiloxane (Product D)

2.23 g of water (2 equivalents, or 0.124 mol) then a catalytic quantity of trifluoroacetic acid (0.1 equivalent, i.e. 6.21 mmol or 0.7 g), to which are added 26 g (0.0621 mol) of bis-(propyldimethylethoxysilane) polysulfide (product C') diluted in 210 ml of dichloromethane are introduced into a 500 ml three-necked flask.

The reaction medium is left stirred at ambient temperature for 24 hours, then dried on magnesium sulfate, filtered and concentrated in a vacuum. Thus 20.5 g of a very viscous pale yellow liquid corresponding majoritarily, according to NMR analysis, to the expected product is isolated, the traces of possible residual solvents being able to be removed by subjecting the product to a vacuum of 200 mm Hg, at a the temperature of 40° C., for 48 h.

The product D thus synthesised appears to be virtually identical to the one obtained previously by hydrolysis (distribution of polysulfides from $x=2$ to $x=6$–average value $x=4.0$–amount of disulfide $S_2$ equal to approximately 17% of the polysulfide units).

III-2. Use as Cross-linking Agent

A) Test 1

The aim of this first test, carried out using a laboratory mixer, is to demonstrate that it is possible to cross-link, without addition of sulfur, a rubber composition using the product D previously synthesised.

Also demonstrated is the improvement in the thermal stability (reversion behaviour) of the compositions based on the polysulfide according to the invention, compared with conventional compositions based on sulfur as cross-linking agent.

The three compositions tested are identical apart from the nature of the cross-linking agent:
 composition C-1: sulfur (1 phr);
 composition C-2: product D (3.7 phr);
 composition C-3: product D (7.5 phr).

Composition C-1 is the control for this test, compositions C-2 and C-3 use the siloxane polysulfide according to the invention in a preferred amount of between 3 and 12 phr.

These compositions are prepared in known manner, as follows: the diene elastomer (or the mixture of diene elastomers, if applicable), the reinforcing filler, then the various other ingredients, with the exception of the cross-linking system comprising at least the siloxane polysulfide (product D) and an accelerator, are introduced into an internal mixer filled to 70%, the initial tank temperature of which is approximately 60° C. Thermomechanical working (non-productive phase) is then performed in one or two steps (total duration of kneading equal to about 7 minutes), until a maximum "dropping" temperature of about 165° C. is reached. The mixture thus obtained is recovered, it is cooled and then the siloxane polysulfide (product D) and the accelerator are added on an external mixer (homo-finisher) at 40° C., by mixing everything (productive phase) for 3 to 4 minutes. The compositions thus obtained are then calendered in the form of sheets (thickness of 2 to 3 mm) or of thin films of rubber in order to measure their physical or mechanical properties, or extruded to form profiled elements which can be used directly, after cutting out and/or assembly to the dimensions desired, as semi-finished products for tires, for example as tire treads.

Tables 1 and 2 show the formulation of the different compositions (Table 1—amounts of the different products expressed in phr), the rheometric properties (at 165° C.) and the evolution of the rheometric torque after 2 hours at 165°

Figure 4:
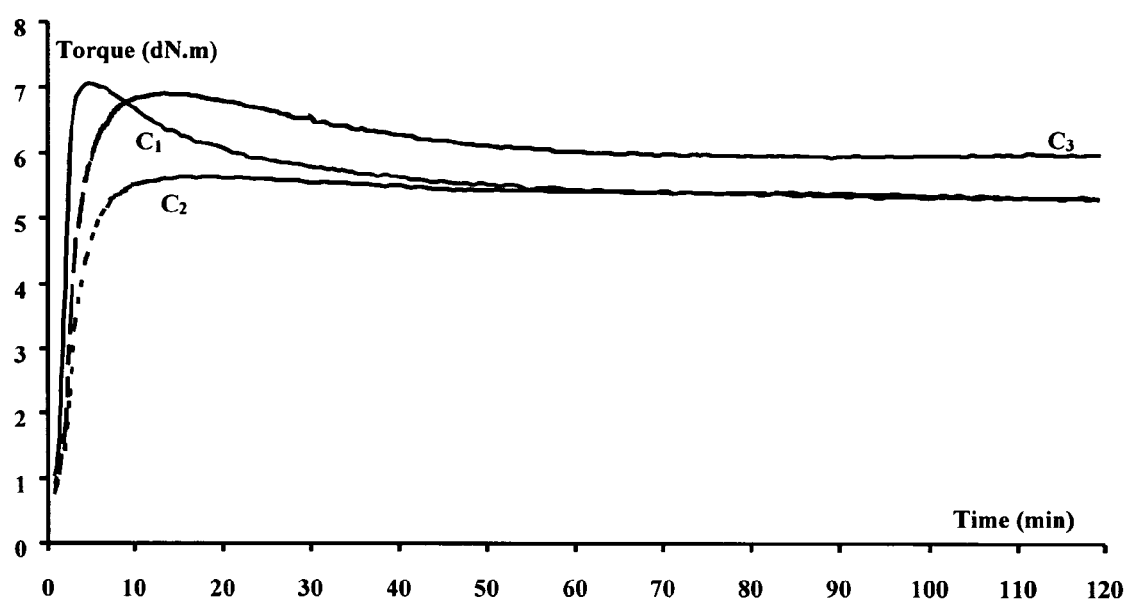
FIG. 4 shows a rheogram (curing curve) for cross-linked rubber compositions.

C., which is representative of the thermal stability of the compositions. FIG. 4 for its part shows the evolution of the rheometric torque (in dN.m) as a function of time (in min), for a temperature of 165° C., curves C1 to C3 corresponding to compositions C-1 to C-3 respectively.

The results of Table 2 demonstrate the unexpected ability of the siloxane polysulfide to cross-link the elastomer chains, as illustrated by the values of $C_{max}$ and Δtorque. Furthermore, the increase in the torque $C_{max}$ and Δtorque with that of the amount of siloxane polysulfide will be noted. The thermal stability (reversion resistance) of compositions C-2 and C-3 is striking, greater than that observed for the control, and this whatever the amount of siloxane polysulfide used, as demonstrated by the losses $ΔR_{60}$ and $ΔR_{120}$ which turn out to be distinctly less than those recorded for the control composition C-1.

FIG. 4 confirms the ability of product D to cross-link the rubber compositions while imparting better reversion resistance thereto. There will be noted in particular the very low reversion (reduction in torque beyond $C_{max}$) for the composition C-2, illustrated both by the parameters $ΔR_{60}$ and $ΔR_{120}$ of Table 2 and by the shape of the curve C2 (existence of a very long vulcanization plateau) of FIG. 4.

B) Test 2

This test confirms the unexpected technical effect as a cross-linking agent of the siloxane polysulfide, and also the improved thermal stability of the rubber compositions, in the presence of various known vulcanization accelerators.

For this, five compositions similar to those of Test 1 above are prepared, these compositions being identical apart from the nature of the cross-linking system (sulfur or siloxane polysulfide, nature of the primary vulcanization accelerator).

Composition C-4 is the control composition (sulfur plus sulfenamide accelerator), and compositions C-5 to C-8 use the siloxane polysulfide according to the invention, with different accelerators.

Tables 3 and 4 show the formulation of these compositions (Table 3—amounts of the different products expressed in phr), and their rheometric properties at 165° C. and the evolution of the rheometric torque after 2 hours at 165° C. (reversion).

A study of the results of Table 4 clearly shows that all the compositions based on siloxane polysulfide exhibit effective cross-linking, whatever the accelerator used or the amount thereof (of between 0.5 and 2.0 phr), with in particular a vulcanization yield Δtorque greater than that of the control. The reversion resistance is distinctly greater for the compositions according to the invention, as illustrated by losses $ΔR_{60}$ and $ΔR_{120}$ which are distinctly less whatever the type of accelerator used.

C) Test 3

This test was carried out on a larger mixer than in the preceding tests, to permit characterization of the rubber compositions in the uncured state and in the cured state, at the curing optimum at 150° C. and after prolonged curing (2 hours at 150° C.).

It confirms the improved thermal stability of the compositions according to the invention, relying on other properties (evolution of the moduli).

For this, two rubber compositions similar to those of Test 1 above, which are identical apart from the cross-linking agent, are compared:
composition C-9 (control): sulfur (1 phr);
composition C-10 (invention): product D (7.5 phr).

Tables 5 and 6 show the formulation of the two compositions, and their properties before curing and after curing at 150° C. The thermal stability of the compositions is characterized by the evolution of the moduli ΔME100 and ΔME300.

It will be noted that the composition according to the invention C-10, compared with composition C-9, not only has no adverse effect on the properties in the uncured state, but on the contrary reveals a distinctly reduced Mooney plasticity, which is synonymous of an improved processing ability in the uncured state. The scorching times T5 are identical for both compositions.

After curing at 150° C. (at the curing optimum), the following are unexpectedly observed for the composition based on the siloxane polysulfide of the invention:

increased values of moduli at high deformation ME100, ME300 and of ratio ME300/ME100, which indicate high-quality reinforcement;

equivalent properties at break;

improved hysteresis properties, as illustrated by significantly lower values of ΔG* and of $\tan(δ)_{max}$, which are favourable to the rolling resistance;

finally, an evolution of the parameters ΔME100 and ΔME300 which confirms the very good thermal stability of the compositions according to the invention, compared with that of the control composition cross-linked conventionally using sulfur.

Thus, owing to the use of a disiloxane polysulfide according to the invention as cross-linking agent, instead of the conventional sulfur, it is possible to combine effective cross-linking and improved thermal stability (reversion resistance).

The invention can be applied particularly advantageously in the rubber compositions usable for the manufacture of finished articles or semi-finished products intended for any suspension system of automotive vehicles, such as tires, internal safety supports for tires, wheels, rubber springs, elastomeric joints, and other suspension and anti-vibration elements.

TABLE 1

|  | Composition No.: | | |
| --- | --- | --- | --- |
|  | C-1 | C-2 | C-3 |
| NR (1) | 100 | 100 | 100 |
| carbon black (2) | 50 | 50 | 50 |
| ZnO (3) | 4 | 4 | 4 |
| stearic acid (4) | 2 | 2 | 2 |
| antioxidant (5) | 2 | 2 | 2 |
| sulfur (6) | 1 | — | — |
| product D (7) | — | 3.7 | 7.5 |
| accelerator (8) | 1 | 1 | 1 |

(1) natural rubber;
(2) N375 (from Cabot);
(3) zinc oxide (industrial grade - from Umicore);
(4) stearin ("Pristerene 4931") from Uniqema;
(5) N-1,3-dimethylbutyl-N-phenyl-para-phenylenediamine ("Santoflex 13" from Flexsys);
(6) sulfur (synthetic sulfur from Solvay);
(7) siloxane polysulfide of formula (II-1) synthesised in accordance with section III-1-A);
(8) N-cyclohexyl-2-benzothiazyl-sulfenamide ("Santocure CBS" from Flexsys).

TABLE 2

| | Composition No.: | | |
|---|---|---|---|
| | C-1 | C-2 | C-3 |
| Rheometric properties (165° C.): | | | |
| $C_{min}$ (dN · m) | 1.03 | 0.93 | 0.77 |
| $C_{max}$ (dN · m) | 7.07 | 5.65 | 6.91 |
| $\Delta$torque (dN · m) | 6.04 | 4.72 | 6.14 |
| $t_i$ (min) | 0 | 1.5 | 1.5 |
| Reversion (2 hours at 165° C.) | | | |
| $\Delta R_{60}$ (%) | −23 | −4 | −12 |
| $\Delta R_{120}$ (%) | −25 | −5 | −13 |

TABLE 3

| | Composition No.: | | | | |
|---|---|---|---|---|---|
| | C-4 | C-5 | C-6 | C-7 | C-8 |
| NR (1) | 100 | 100 | 100 | 100 | 100 |
| carbon black (2) | 50 | 50 | 50 | 50 | 50 |
| ZnO (3) | 4 | 4 | 4 | 4 | 4 |
| stearic acid (4) | 2 | 2 | 2 | 2 | 2 |
| antioxidant (5) | 2 | 2 | 2 | 2 | 2 |
| sulfur (6) | 1 | — | — | — | — |
| product D (7) | — | 7.5 | 7.5 | 7.5 | 7.5 |
| CBS accelerator (8) | 1 | 1 | — | — | — |
| TBBS accelerator (9) | — | — | 0.9 | — | — |
| TBSI accelerator (10) | — | — | — | 1.5 | — |
| MBTS accelerator (11) | — | — | — | — | 1.3 |

(1) to (8) idem Table 1;
(9) N-tert.-butyl-2-benzothiazyl-sulfenamide ("Santocure TBBS" from Flexsys);
(10) N-tert.-butyl-2-benzothiazyl-sulfenimide ("Santocure TBSI" from Flexsys);
(11) 2-mercaptobenzothiazyl disulfide ("Perkacit MBTS" Flexsys).

TABLE 4

| | Composition No.: | | | | |
|---|---|---|---|---|---|
| | C-4 | C-5 | C-6 | C-7 | C-8 |
| Rheometric properties (165° C.): | | | | | |
| $C_{min}$ (dN · m) | 0.97 | 0.80 | 0.84 | 0.76 | 0.84 |
| $C_{max}$ (dN · m) | 6.85 | 7.24 | 7.39 | 8.72 | 7.17 |
| $\Delta$torque (dN · m) | 5.88 | 6.44 | 6.55 | 7.96 | 6.33 |
| $t_i$ (min) | 0 | 1.7 | 1.9 | 2.0 | 0.8 |
| Reversion (2 hours at 165° C.) | | | | | |
| $\Delta R_{60}$ (%) | −24 | −10 | −7 | −4 | −5 |
| $\Delta R_{120}$ (%) | −26 | −14 | −10 | −5 | −7 |

TABLE 5

| | Composition No.: | |
|---|---|---|
| | C-9 | C-10 |
| NR (1) | 100 | 100 |
| carbon black (2) | 50 | 50 |
| ZnO (3) | 4 | 4 |
| stearic acid (4) | 2 | 2 |
| antioxidant (5) | 2 | 2 |
| sulfur (6) | 1 | — |
| product D (7) | — | 7.5 |
| accelerator (8) | 1 | 1 |

(1) to (8) idem Table 1.

TABLE 6

| | Composition No.: | |
|---|---|---|
| | C-9 | C-10 |
| Properties before curing: | | |
| Mooney (MU) | 83 | 62 |
| T5 (min) | 16 | 16 |
| Properties after curing (optimum at 150° C.): | | |
| ME10 (MPa) | 4.5 | 4.6 |
| ME100 (MPa) | 1.8 | 2.0 |
| ME300 (MPa) | 2.5 | 2.7 |
| ME300/ME100 | 1.35 | 1.38 |
| $\Delta G^*$ | 2.74 | 2.43 |
| $\tan(\delta)_{max}$ | 0.215 | 0.193 |
| breaking stress (MPa) | 29.5 | 28.8 |
| elongation at break (%) | 561 | 546 |
| Reversion (2 hours at 150° C.): | | |
| $\Delta$ME100 (%) | −10 | −3 |
| $\Delta$ME300 (%) | −13 | −4 |

What is claimed is:

1. Siloxane polysulfide compound of the general formula:

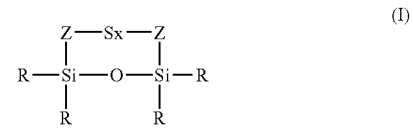

in which:
- the number x, which may be an integer or a fractional number, is greater than 2;
- the radicals Z, which may be identical or different, are divalent bond groups;
- the radicals R, which may be identical or different, are hydrocarbon groups.

2. The compound according to claim 1, wherein the radicals R are selected from the group which consists of hydrocarbon groups and the groups Z are selected from the group which consists of divalent bond groups, each comprising 1 to 18 carbon atoms.

3. The compound according to claim 2, wherein the radicals R are selected from the group which consists of $C_1$–$C_6$ alkyls, $C_5$–$C_8$ cycloalkyls and the phenyl radical; and the groups Z are selected from the group which consists of $C_1$–$C_{18}$ alkylenes and $C_6$–$C_{12}$ arylenes.

4. The compound according to claim 3, wherein the radicals R are selected from the group which consists of $C_1$–$C_6$ alkyls and the groups Z are selected from the group which consists of $C_1$–$C_{10}$ alkylenes.

5. The compound according to claim 4, wherein the radicals R are selected from the group which consists of $C_1$–$C_3$ alkyls, and the groups Z are selected from the group which consists of $C_1$–$C_4$ alkylenes.

6. The compound according to claim 5, wherein the groups Z are selected from the group which consists of $C_2$–$C_4$ alkylenes.

7. The compound according to claim 6, wherein the siloxane polysulfide corresponds to the formula (II):

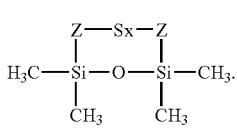

(II)

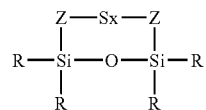

(I)

8. The compound according to claim 7, wherein Z represents the propylene group.

9. The compound according to claim 1, wherein x is between 3 and 5.

10. A process for obtaining a siloxane polysulfide according to claim 1, wherein said process comprises the following steps:

a) starting from a halogenated organosilane (hereafter product A) of formula (Hal=halogen):

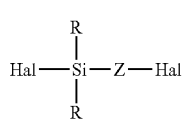

(A)

b) subjecting it either to alcoholysis by action of an alcohol R'—OH (R'=hydrocarbon radical) or to hydrolysis by action of water in an inert organic solvent, in both cases in the presence of an organic base to trap the acid halide formed, in order to obtain (hereafter product B) either a monoalkoxysilane (in this case, R' is the hydrocarbon radical in formula (B)), or a monohydroxysilane (in this case, R' is H in formula (B)), of formula:

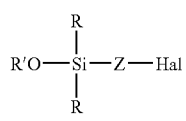

(B)

c) sulfurizing product B by action of a polysulfide, in order to obtain as intermediate product (hereafter product C) an alkoxysilane or hydroxysilane polysulfide of formula:

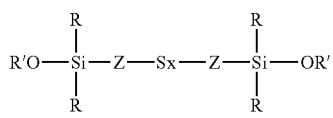

(C)

d) then performing a cyclization step on product C to produce the desired product of formula (I):

in which:
the number x, which may be an integer or a fractional number, is greater than 2;
the radicals Z, which may be identical or different, are divalent bond groups;
the radicals R, which may be identical or different, are hydrocarbon groups.

11. The process according to claim 10, wherein Hal is bromine or chlorine.

12. The process according to claim 10, wherein R' is selected from the group which consists of H and $C_1$–$C_6$ alkyls.

13. The process according to claim 12, wherein R' is selected from the group which consists of $C_1$–$C_3$ alkyls.

14. The process according to claim 10, wherein the alcoholysis is carried out at a temperature which is less than 15° C.

15. The process according to claim 10, wherein the organic base intended to trap the acid halide formed, is a tertiary amine.

16. The process according to claim 10, wherein step (b) consists of hydrolysis of product A.

17. The process according to claim 10, wherein the polysulfide of step (d) is an ammonium or a metal polysulfide.

18. The process according to claim 17, wherein the ammonium or metal polysulfide has the formula $M_2S_X$ or $M'S_X$ (M=alkali metal or $NH_4$; M'=Zn or alkaline-earth metal).

19. The process according to claim 18, wherein the metal polysulfide is a sodium polysulfide $Na_2S_X$.

20. The process according to claim 17, wherein the sulfurization step is carried out in aqueous phase.

21. The process according to claim 20, wherein the sulfurization step is carried out in a two-phase medium water/organic solvent.

22. The process according to claim 21, wherein the sulfurization step is carried out in the presence of a phase transfer catalyst.

23. The process according to claim 22, wherein the sulfurization step is carried out in the presence of a salt of formula M"Hal or M"$_2SO_4$, M" being selected from among Li, Na and K and Hal being selected from among F, Cl and Br.

24. The process according to claim 10, wherein the cyclization step d) is carried out in acid medium.

* * * * *